United States Patent
Kakuda et al.

(10) Patent No.: US 8,093,289 B2
(45) Date of Patent: Jan. 10, 2012

(54) ORAL COMPOSITION COMPRISING 3-[5-[4-(CYCLOPENTYLOXY)-2-HYDROXYBENZOYL]-2-[(3-HYDROXY-1,2-BENZISOXAZOL-6-YL)METHOXY]PHENYL] PROPIONIC ACID OR SALT THEREOF

(75) Inventors: Sahoe Kakuda, Toyama (JP); Tatsuhito Yahata, Toyama (JP); Masashi Kaneko, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 495 days.

(21) Appl. No.: 12/302,380

(22) PCT Filed: May 25, 2007

(86) PCT No.: PCT/JP2007/060671
§ 371 (c)(1),
(2), (4) Date: Nov. 25, 2008

(87) PCT Pub. No.: WO2007/138997
PCT Pub. Date: Dec. 6, 2007

(65) Prior Publication Data
US 2009/0163562 A1    Jun. 25, 2009

(30) Foreign Application Priority Data
May 26, 2006 (JP) .................. 2006-146257
May 26, 2006 (JP) .................. 2006-146315

(51) Int. Cl.
*A01N 43/16* (2006.01)
*A61K 47/32* (2006.01)
(52) U.S. Cl. .............. 514/456; 514/459; 514/772.3
(58) Field of Classification Search .......... None
See application file for complete search history.

(56) References Cited

U.S. PATENT DOCUMENTS 3,670,080 A * 6/1972 Hirata ................. 514/172
2005/0113400 A1 5/2005 Chaki et al.

FOREIGN PATENT DOCUMENTS

| CA | 2467261 C | * 11/2002 |
|---|---|---|
| JP | 55 129221 | 10/1980 |
| JP | 56 110612 | 9/1981 |
| JP | 59 42313 | 3/1984 |
| JP | 60 190723 | 9/1985 |
| WO | 03 042150 | 5/2003 |

OTHER PUBLICATIONS

Usui, Technology to improve dissolution characteristics of poorly soluble drug, In Particulate Design and Pharmaceutical Technology that Are Useful Now, The Society of Powder Technology, Japan/Division of Particulate Preparation and Design (ed.), First edition, pp. 205-211, 2003.*
U.S. Appl. No. 12/934,572, filed Sep. 24, 2010, Aikawa, et al.
U.S. Appl. No. 12/989,029, filed Oct. 21, 2010, Aikawa, et al.
"Particulate Design and Pharmaceutical Technology", Edited by the Society of Powder Technology, Japan/Division of Particulate Design and Preparations, First Edition, pp. 205-211, (2003).

* cited by examiner

*Primary Examiner* — Sreeni Padmanabhan
*Assistant Examiner* — Svetlana M Ivanova
(74) *Attorney, Agent, or Firm* — Oblon, Spivak, McClelland, Maier & Neustadt, L.L.P.

(57) ABSTRACT

An oral composition contains 3-{5-[4-(cyclopentyloxy)-2-hydroxybenzoyl]-2-[(3-hydroxy-1,2-benzisoxazol-6-yl) methoxy]phenyl}propionic acid or a salt thereof and polyvinylpyrrolidone is advantageous as an oral medication composition (1) which can be produced without requiring new manufacturing equipment; (2) which can be produced with simple steps; (3) which maintains stable solubility even with changes in the pH of the gastrointestinal tract and of which gastrointestinal tract absorption is improved.

16 Claims, No Drawings

ORAL COMPOSITION COMPRISING 3-[5-[4-(CYCLOPENTYLOXY)-2-HYDROXYBENZOYL]-2-[(3-HYDROXY-1,2-BENZISOXAZOL-6-YL)METHOXY]PHENYL] PROPIONIC ACID OR SALT THEREOF

TECHNICAL FIELD

The present invention relates to an oral composition containing 3-{5-[4-(cyclopentyloxy)-2-hydroxybenzoyl]-2-[(3-hydroxy-1,2-benzisoxazol-6-yl)methoxy]phenyl}propionic acid or a salt thereof and polyvinylpyrrolidone.

BACKGROUND ART

3-{5-[4-(cyclopentyloxy)-2-hydroxybenzoyl]-2-[(3-hydroxy-1,2-benzisoxazol-6-yl)methoxy]phenyl}propionic acid (henceforth referred as T-5224) or a salt thereof is a compound in development as a therapeutic agent for inflammatory diseases targeting transcription factor AP-1 (Patent Document 1).

T-5224 is a hardly-soluble medication with low solubility in the secretions inside the gastrointestinal tract (in the range from acidic to neutral). As a result, when solid T-5224 is administered orally, the absorption from the gastrointestinal tract is not adequate. In addition, when a basic solution of T-5224 is administered orally, due to the change of solution property by secretion inside the gastrointestinal tract, T-5224 precipitates, and an adequate absorption is not achieved.

For improving the solubility of hardly-soluble medications, various pharmaceutical technologies have been studied. For example, (1) a method for improving the solubility by making a salt of the hardly-soluble medication, (2) a method for making amorphous, (3) a method for making soluble by forming a cyclodextrin clathrate (4) a method for making soluble by adding a surface active agent (5) a method for dissolving in a solvent with affinity for the hardly-soluble medication (for example, Macrogol and propylene glycol, and the like) (6) a method for making fine particles (Non-Patent Document 1).

However, (1) due to the change of solution property by secretion inside the gastrointestinal tract, the salt of T-5224 precipitates; (2) with a method for making soluble by adding a surface active agent, damage to the gastrointestinal tract due to the surface active agent is a concern; (3) with regard to the method for making amorphous, a method for making a cyclodextrin clathrate, and a method for making fine particles, these require special manufacturing devices and complex processes, and manufacture is not easy; (4) with regard to a method for dissolving in solvents that have affinity with the hardly-soluble medications, there is concern that there may be side-effects from the solvents, and furthermore for making soft gelatins and the like, a special manufacturing device and complex processes become necessary, and the manufacturing is not easy.

Formulations of T-5224 or a salt thereof that have good absorption through oral administration and that can be produced easily are not known.

Patent Document 1: International Publication 03/042150 pamphlet

Non-Patent Document 1: Edited by The Society of Powder Technology, Japan/Division of Particulate Design and Preparations "Particle Design and Pharmaceutical Technology that are useful now" First edition, Jiho, Inc., Sep. 1, 2003, p. 205-211.

DISCLOSURE OF THE INVENTION

There is desired an oral composition (1) which can be produced without requiring new manufacturing equipment; (2) which can be produced with simple steps; (3) which maintains stable solubility even with changes in the pH of the gastrointestinal tract and of which gastrointestinal tract absorption is improved.

Means for Solving the Problems

Under these conditions, the present inventors conducted intensive research and discovered that with an oral composition in which polyvinylpyrrolidone is added to T-5224, the absorption of T-5224 is greatly improved even in the neutral range where there is low solubility. Especially, with an oral solid composition in which polyvinylpyrrolidone and a basic material of which the 5 w/v % aqueous solution has the pH of 10 or more are added to T-5224 and an oral aqueous solution in which polyvinylpyrrolidone is added to T-5224, the absorption of T-5224 was found to be greatly improved, and the present inventors had completed the present invention.

Advantages of the Invention

The T-5224 oral composition containing the polyvinylpyrrolidone of the present invention is advantageous as an oral medication composition (1) which can be produced without requiring new manufacturing equipment; (2) which can be produced with simple steps; (3) which maintains stable solubility even with changes in the pH of the gastrointestinal tract and of which gastrointestinal tract absorption is improved.

BEST MODE FOR CARRYING OUT THE INVENTION

The present invention will be described in detail below.
The % used in the present description is % by weight unless otherwise noted. w/v % is the weight/volume % at 20° C. The pH is the value at 20° C.

The medicinal composition of the present invention is an oral composition containing T-5224 or a salt thereof and polyvinylpyrrolidone (PVP).

More specifically, the present invention is an oral solid composition containing T-5224 or a salt thereof, polyvinylpyrrolidone, and a basic material of which the 5 w/v % aqueous solution has the pH of 10 or more. The present invention is also an oral aqueous solution containing T-5224 or a salt thereof and polyvinylpyrrolidone.

Compared to the medicinal composition which does not contain polyvinylpyrrolidone and a basic material, the oral solid composition of the present invention had improved and maintained solubility of the hardly-soluble T-5224 in the neutral range, and absorption was greatly improved.

The T-5224 or a salt thereof used in the present invention can be produced by the method described in International Publication Number 03/042150 pamphlet, for example.

The amount of T-5224 contained in the oral solid composition of the present invention is 0.1-50% of the composition, and preferably 1-30%.

With regard to the T-5224 or a salt thereof, when isomers are present (for example, geometric isomers and tautomers and the like), the present invention includes these isomers, and the present invention also includes solvates, hydrates, and various crystalline forms.

Examples of the "basic material of which the 5 w/v % aqueous solution has the pH of 10 or more" include sodium hydroxide, potassium hydroxide, sodium carbonate, potassium carbonate, meglumine, arginine, and arginine hydrates, and salts thereof, and the like. Preferred examples include L-arginine and a hydrate thereof, and potassium carbonate. More preferred examples include L-arginine and a hydrate thereof.

For substances having optical isomers such as arginine and the like, this can be the optical isomers such as L-isomer or D-isomer, mixtures thereof, and hydrates thereof.

The mixture amount for the basic material is 0.1-30 weight parts with respect to T-5224, and preferably 0.5 to 10 weight parts, and more preferably 1 to 6 weight parts.

The polyvinylpyrrolidone used in the oral solid composition of the present invention is not particularly limited, but examples include polyvinylpyrrolidone K-30, polyvinylpyrrolidone K-25 and polyvinylpyrrolidone K-17, and the like.

The mixture amount of polyvinylpyrrolidone is 0.1-30 weight parts with respect to T-5224 and is preferably 0.1-6 weight parts, and more preferably 0.3 to 3 weight parts.

In the oral solid composition of the present invention, an excipient can be further added.

Examples of excipients include sugar alcohols such as erythritol, mannitol, xylitol, and sorbitol, and the like; sugars such as white soft sugar, powdered sucrose, lactose, and glucose and the like; cyclodextrins, such as α-cyclodextrin, β-cyclodextrin, γ-cyclodextrin, hydroxypropyl β-cyclodextrin, and sulfobutyl ether β-cyclodextrin sodium, and the like; cellulose such as crystalline cellulose and microcrystalline cellulose, and the like; and starches such as corn starch, potato starch, and pregelatinized starch, and the like. With regard to these excipients, one type or two or more types in combination can be added. Preferable excipients include water-soluble excipients such as sugar alcohols, sugars, and cyclodextrins, and the like. For sugar alcohols, mannitol, for sugars, lactose, for cyclodextrins, β-cyclodextrin and hydroxypropyl β-cyclodextrin are further preferred.

The amount of excipient added is not particularly limited, and an amount corresponding to the formulation is added.

In the oral solid composition of the present invention, additives that are typically used in medications can be used within the range that does not interfere with the effect of the present invention. For such additives, examples include disintegrants, binding agents, lubricants, taste correctives, colorants, flavoring agents, surface active agents, coating agents, and plasticizers and the like.

Examples of disintegrants include carmellose, carmellose calcium, croscarmellose sodium, sodium starch glycolate, crospovidone, low substituted hydroxypropyl cellulose and partly pregelatinized starch, and the like.

Examples of the binding agents include hydroxypropyl cellulose, carmellose sodium, and methyl cellulose, and the like.

Examples of lubricants include stearic acid, magnesium stearate, calcium stearate, talc, hydrated silicon dioxide, light anhydrous silicic acid, and sucrose esters of fatty acids, and the like.

Examples of taste correctives include aspartame, saccharine, stevia, thaumatin, and acesulfame potassium and the like.

Examples of colorants include titanium dioxide, red ferric oxide, yellow ferric oxide, black iron oxide, food red No. 102, food yellow No. 4, and food yellow No. 5, and the like.

Examples of flavoring agents include essential oils such as orange oil, lemon oil, mint oil, and pine oil, and the like; essences such as orange essence, peppermint essence, and the like; flavors such as cherry flavor, vanilla flavor, fruit flavor, and the like; powder aromatic materials such as apple micron, banana micron, peach micron, strawberry micron, and orange micron, and the like; and vanillin and ethyl vanillin, and the like.

Examples of surface active agents include sodium lauryl sulfate, dioctyl sodium sulfosuccinate, polysorbate and polyoxyethylene hydrogenated castor oil, and the like.

Examples of coating agents include hydroxypropyl methylcellulose, aminoalkyl methacrylate copolymer E, aminoalkyl methacrylate copolymer RS, ethylcellulose, cellulose acetate phthalate, hydroxymethyl cellulose phthalate, methacrylic acid copolymer L, methacrylic acid copolymer LD, and methacrylic acid copolymer S, and the like.

Examples of plasticizers include triethyl citrate, Macrogol, triacetin, and propylene glycol, and the like.

These additives are used singly or two or more types are combined and used. The addition amounts are not particularly limited, and depending on the objective, these can be mixed so that their effects are adequately expressed.

Using formulation additives such as medically allowable excipients, carriers, and diluents, and the like as needed, the oral solid composition of the present invention can be used as a formulation in tablets, capsules, granules, fine powders, powders, rapid disintegrating tablets, formulations that are dissolved before use, dry syrups, or powder formulations, and the like. With the composition of the present invention, in order to have T-5224 which is a hardly-soluble substance dissolved within the gastrointestinal tract and to maintain this condition, the T-5224, the basic material, and the polyvinylpyrrolidone which are the constituents are preferably in close contact. For example, tablets, capsules, and formulations which have passed through a granulation process (granules, fine granules, powders, rapid disintegrating tablets, formulations which are dissolved before use, dry syrup or powder formulations, and the like) are preferred. More preferred are tablets and capsules. Further preferred are tablets.

The method of administration, dosage, and dosage frequency are selected according to the age of patients, body weight, and symptoms. Normally, the amount for exhibiting the medical effect is administered once to divided over several times per day, and for a normal adult, for T-5224, 1-2000 mg is administered divided over one time or over several times per day.

The method for making the oral solid composition of the present invention into a formulation is not particularly limited and is implemented by the normal methods. In the case of tablets, examples include methods in which tablet press is conducted after creating granulated material by fluidized bed granulation, wet granulation, agitation granulation, dry granulation, extruding granulation or the like, and a direct tablet press method in which the composition is mixed and tablet press is conducted directly. In the case of capsules, examples include methods in which capsules are filled with granulated material or directly with the composition. The oral solid composition of the present invention can be pulverized and used if necessary.

When producing tablets, the direct tablet press method is preferred, and a direct tablet pressing method which uses water-soluble directly compressible excipients is more preferred. The water-soluble directly compressible excipients include directly compressible lactose, directly compressible mannitol, directly compressible sorbitol and the like.

For the directly compressible excipient, directly compressible mannitol is preferably used.

When producing by the direct tablet press method using L-arginine as the basic material of which the 5 w/v % aqueous solution has the pH of 10 or more, preferably, tablet pressing is conducted using L-arginine hydrate or a moisturized product of L-arginine, and then drying this. Further preferred is conducting tablet pressing using L-arginine hydrate or moisturized product of L-arginine and moisturized product of polyvinylpyrrolidone, and then drying. By tablet pressing using L-arginine hydrate or a moisturized product of L-arginine, physical stability such as tablet hardness and the like is improved.

Compared to the oral aqueous solution containing solubilizers or solubilizing agents such as hydroxypropyl methylcellulose and polyethylene glycol 6000, the oral aqueous solution of the present invention has greatly improved solubility maintenance effect and stability with respect to changes in pH, and furthermore, the absorption of T-5224 is greatly improved.

The T-5224 or a salt thereof used in the oral aqueous solution of the present invention is produced according to the method described in International Publication Number 03/042150 pamphlet.

The amount of T-5224 contained in the oral aqueous solution of the present invention is 0.001-50 w/v % with respect to the oral aqueous solution, preferably 0.01-20 w/v %.

With regard to the T-5224 or a salt thereof, when isomers are present (for example, geometric isomers and tautomers and the like), the present invention includes these isomers, and the present invention also includes solvates, hydrates, and various crystalline forms.

The polyvinylpyrrolidone used in the oral solid composition of the present invention is not particularly limited, but examples include polyvinylpyrrolidone K-30, polyvinylpyrrolidone K-25 and polyvinylpyrrolidone K-17, and the like. The mixing amount of polyvinylpyrrolidone is 0.1-100 weight parts with respect to T-5224 or the salt thereof and is preferably 0.5-20 weight parts, and more preferably 1 to 10 weight parts.

The oral aqueous solution of the present invention can be formulated by the standard methods and is not limited. For example, T-5224 or a salt thereof and polyvinylpyrrolidone are dissolved in an aqueous solvent. Preferably, this is dissolved in an aqueous solvent in which a basic material is dissolved. Examples of basic material include potassium hydroxide, sodium hydroxide, magnesium hydroxide, sodium bicarbonate, sodium lactate, sodium citrate, and L-arginine, and the like.

In addition, the pH of the resulting aqueous solution can be adjusted with a pH adjuster.

The pH of the oral aqueous solution of the present invention is preferably 1 to 10, and more preferably 3 to 9.

In the oral aqueous solution of the present invention, additives that are typically used in medications can be used within the range that does not interfere with the effect of the present invention. For such additives, examples include pH adjusters, taste correctives, flavoring agents, surface active agents, and solubilizers and the like.

Examples of pH adjusters include hydrochloric acid, citric acid, glycine, succinic acid, acetic acid, tartaric acid, lactic acid, and maleic acid, and the like.

Examples of taste correctives include aspartame, saccharine, stevia, thaumatin, and acesulfame potassium and the like.

Examples of flavoring agents include essential oils such as orange oil, lemon oil, mint oil, and pine oil, and the like; essences such as orange essence, peppermint essence, and the like; flavors such as cherry flavor, vanilla flavor, fruit flavor, and the like; aromatic powder such as apple micron, banana micron, peach micron, strawberry micron, and orange micron, and the like; and vanillin and ethyl vanillin, and the like.

Examples of surface active agents include sodium lauryl sulfate, dioctyl sodium sulfosuccinate, polysorbate and polyoxyethylene hydrogenated castor oil, and the like.

Examples of solubilizers include purified water, ethanol, propylene glycol, polyethylene glycol, glycerin, and the like.

These additives are used singly or two or more types are combined and used. The mixing amounts are not particularly limited, and depending on the objective, these can be mixed so that their effects are adequately expressed.

Using formulation additives such as medically allowable excipients, carriers, and diluents, and the like as needed, the oral aqueous solution of the present invention can be used as a formulation in solutions, syrups, lemonades, and the like. In addition, the method of administration, dosage, and dosage frequency are selected according to the age of patients, body weight, and symptoms. Normally, the amount for exhibiting the medical effect is administered once to divided over several times per day, and for a normal adult, for T-5224, 1-2000 mg is administered divided over one time or over several times per day.

Next, the advantages of the present invention are explained with the following test examples.

TEST EXAMPLE 1

Dissolution Test (Oral Solid Composition)

For the samples, the composition of example 1 and the compositions of Comparative examples 1 to 3 were used. All of the samples are tablets containing 10 mg of T-5224.

The test was conducted according to the Japanese Pharmacopoeia dissolution test paddle method, the paddle revolution number was 50 rpm. The samples were placed in 250 mL of the 1st Fluid for disintegration test of the Japanese Pharmacopoeia, and this was stirred for 30 minutes (test solution pH 1.2). This was a method in which the pH was changed over time by adding, after 30 minutes, 125 mL of 0.2 mol/L disodium hydrogenphosphate (test solution pH 5.6), and after a further 30 minutes, adding 125 mL (test sample pH 6.8). The sample solution was collected periodically. The dissolution rate (%) of T-5224 was determined by optical density method. The results are shown in Table 1.

TABLE 1

| | time of dissolution | | |
| --- | --- | --- | --- |
| sample | 15 minutes (pH 1.2) | 45 minutes (pH 5.6) | 90 minutes (pH 6.8) |
| example 1 | 18.5 | 61.9 | 53.8 |
| comparative example 1 | 0.1 | 0.5 | 9.3 |
| comparative example 2 | 0.3 | 0.8 | 8.4 |
| comparative example 3 | 0.2 | 1.6 | 22.9 |

The tablet of example 1 containing T-5224, polyvinylpyrrolidone, and L-arginine showed good dissolution in test solutions in the acidic and neutral range as compared to the tablet of Comparative example 1 which does not contain polyvinylpyrrolidone and L-arginine, and the tablet of Comparative example 2 which contains polyvinylpyrrolidone and does not contain L-arginine, and the tablet of Comparative example 3 which contains L-arginine and does not contain polyvinylpyrrolidone.

TEST EXAMPLE 2

Dissolution Test (Oral Solid Composition)

For the samples, the composition of example 2, composition of example 3, and compositions of Comparative examples 4-7 were used. All of the samples were tablets containing 10 mg of T-5224.

The same pH varying dissolution test was conducted as in the test example 1. The results are shown in Table 2.

TABLE 2

| sample | time of dissolution | | |
|---|---|---|---|
| | 15 minutes (pH 1.2) | 45 minutes (pH 5.6) | 90 minutes (pH 6.8) |
| example 2 | 55.9 | 81.1 | 93.3 |
| example 3 | 47.1 | 68.3 | 76.2 |
| comparative example 4 | 6.1 | 10.6 | 20.6 |
| comparative example 5 | 0.1 | 2.1 | 14.3 |
| comparative example 6 | 0.1 | 1.6 | 11.4 |
| comparative example 7 | 1.4 | 10.4 | 18.3 |

The composition of example 2 in which L-arginine is added as the basic material and the composition of example 3 in which potassium carbonate is added exhibited improved dissolution as compared to the composition of Comparative example 4 in which sodium bicarbonate, which is a basic material of which the 5 w/v % solution has pH of less than 10, is added, the composition of Comparative example 5 in which glycine, which is a weakly acidic water-soluble additive, is added, and the compositions of Comparative example 6 and Comparative example 7 in which anhydrous dibasic calcium phosphate and magnesium aluminometasilicate, which are basic material that do not dissolve in water, are added.

TEST EXAMPLE 3

Dissolution Test (Oral Solid Composition)

For the samples, the compositions of examples 8-11 and Comparative example 9 and Comparative example 10 were used. All of the samples were tablets or capsules containing 10 mg of T-5224.

The test was conducted according to the Japanese Pharmacopoeia dissolution test paddle method. The paddle revolution number was 50 rpm. The samples were placed in 900 mL of a McIlvaine buffer solution of pH 6.8 and stirred for 30 minutes. Test solutions were collected periodically, and the dissolution rate (%) of T-5224 were determined by spectrophotometry. The McIlvaine buffer solution of pH 6.8 was prepared using 0.1 mol/L citric acid and 0.2 mol/L dibasic sodium phosphate and adjusting to pH 6.8, and the results are shown in Table 3.

TABLE 3

| sample | time of dissolution | |
|---|---|---|
| | 15 minutes | 30 minutes |
| example 8 | 85.1 | 83.2 |
| example 9 | 86.0 | 85.1 |
| example 10 | 74.8 | 91.7 |
| example 11 | 78.7 | 76.1 |
| comparative example 9 | 57.8 | 61.3 |
| comparative example 10 | 0.0 | 1.4 |

The compositions in which polyvinylpyrrolidone was added at a weight ratio of 0.3 times weight (example 11), 0.5 times weight (example 8), 1 time weight (example 9), 3 times weight (Embodiment 10) exhibited improved dissolution as compared to the composition of Comparative example 9, in which L-arginine is added at three times weight with respect to T-5224 and in which no polyvinylpyrrolidone is added, and the composition of Comparative example 10 in which a capsule is filled with T-5224.

TEST EXAMPLE 4

Dissolution Test (Oral Solid Composition)

For the samples, the compositions of examples 17 and 18 were used. Both are capsules containing 20 mg of T-5224.

The test was conducted according to the Japanese Pharmacopoeia dissolution test paddle method. The paddle revolution number was 50 rpm. The samples were placed in 900 mL of a buffer solution adjusted to pH 6.8 using 0.025 mol/L citric acid and 0.05 mol/L dibasic sodium phosphate, and this was stirred for 30 minutes. Test solutions were collected periodically, and the dissolution rate (%) of T-5224 was determined by spectrophotometry. The results are shown in Table 4.

TABLE 4

| sample | time of dissolution | |
|---|---|---|
| | 15 minutes | 30 minutes |
| example 17 | 90.9 | 93.2 |
| example 18 | 84.0 | 86.5 |

Both the compositions of example 17, in which directly compressible mannitol is added as an excipient, and example 18 in which corn starch is added showed good dissolution.

TEST EXAMPLE 5

Dissolution Test (Oral Solid Composition)

For the samples, the compositions of examples 19, 20 and 22 were used. They are capsules containing 80 mg and 40 mg of T-5224, and a tablet containing 40 mg of T-5224.

The same dissolution test as in Test example 4 was conducted. The results are shown in Table 5.

TABLE 5

| sample | time of dissolution | |
|---|---|---|
| | 15 minutes | 30 minutes |
| example 19 | 92.6 | 85.4 |
| example 20 | 93.1 | 97.5 |
| example 22 | 82.8 | 99.2 |

The tablet of example 22 and the capsule of example 20, which contain 40 mg of T-5224, and the capsule of example 19, which contains 80 mg of T-5224, all exhibited good dissolution.

TEST EXAMPLE 6

Oral Administration Test for Dogs (Oral Solid Composition)

For the samples, the compositions of examples 4 to 10 and Comparative example 8 were used.

Male beagles (n=4 to 6 dogs) of weight 10-15 kg were fasted for approximately 17 hours from the day before drug administration. With the samples of examples 4-10, 10 mg/kg of T-5224 and with the sample of Comparative example 8, 30 mg/kg of T-5224 were administered orally. After administration, the dogs ingested 20 mL of water. Blood was collected periodically from the front leg vein, and after removing the protein from the obtained plasma with acetonitrile, the concentration of T-5224 was measured by the LC-MS/MS method. The area under the curve (AUC) value for the plasma concentration-time curve for 0 to 6 hours was determined. The unit for the AUC value is μg·hr/mL. The results are shown in Table 6.

TABLE 6

| sample | composition of administration (ratio of material contained) T-5224:PVP:L-arginine | dose of administration (mg/kg) | $AUC_{0-6}$ (μg · hr/mL) |
| --- | --- | --- | --- |
| example 4 | 1:3:6 | 10 | 0.72 |
| example 5 | 1:3:3 | 10 | 0.66 |
| example 6 | 1:3:2 | 10 | 0.35 |
| example 7 | 1:3:1 | 10 | 0.25 |
| example 8 | 1:0.5:3 | 10 | 0.83 |
| example 9 | 1:1:3 | 10 | 0.71 |
| example 10 | 1:3:3 | 10 | 0.52 |
| comparative example 8 | capsule filling of original drug | 30 | 0.13 |

Compared to the Comparative example 8 in which a dosage of 30 mg/kg was administered orally, the oral solid compositions of the present invention (examples 4-10) in which 10 mg/kg were administered orally had greatly increased AUC values.

TEST EXAMPLE 7

Solubility in Neutral (Oral Aqueous Solutions)

For the samples, the compositions of examples 27 to 29 and the compositions of Comparative examples 11 to 13 were used. All are solutions containing 10 mg/mL of T-5224.

Each sample was diluted with pH 6.8 buffer solution (prepared using 0.1 mol/L citric acid and 0.2 mol/L dibasic sodium phosphate) so that the T-5224 concentration was approximately 100 μg/mL. These solutions were left standing in a 37° C. water bath, and centrifugation was conducted after 1 hour. The concentration (μg/mL) of T-5224 in the supernatant was measured using high performance liquid chromatography. The results are shown in Table 7.

TABLE 7

| | time of allowing to stand | |
| --- | --- | --- |
| sample | 0 hr | 1 hr |
| example 27 | 98.8 | 98.1 |
| example 28 | 104.4 | 101.7 |
| example 29 | 103.1 | 103.6 |
| comparative example 11 | 5.9 | 8.2 |
| comparative example 12 | 20.8 | 20.4 |
| comparative example 13 | 8.6 | 9.7 |

All of the solutions of examples 27 to 29, which contain polyvinylpyrrolidone, maintained solubility even when diluted with pH 6.8 buffer solution as compared to the solutions of Comparative example 11, which does not contain additives, Comparative example 12, which contains hydroxypropyl methylcellulose, and Comparative example 13, which contains Macrogol 6000.

TEST EXAMPLE 8

Dissolution Test (Oral Aqueous Solution)

For the samples, the compositions of examples 30-35 and the compositions of Comparative examples 14 to 15 were used.

The test was conducted according to the Japanese Pharmacopoeia dissolution test paddle method, the paddle revolution number was 50 rpm. The samples which contain 10 mg of T-5224 were placed in 250 mL of the 1st Fluid for disintegration test of the Japanese Pharmacopoeia, and this was stirred for 30 minutes (test solution pH 1.2). This was a method in which the pH was changed over time by adding, after 30 minutes, 125 mL of 0.2 mol/L dibasic sodium phosphate (test solution pH 5.6), and after a further 30 minutes, adding 125 mL (test sample pH 6.8). The sample solution was collected periodically. The dissolution rate (%) of T-5224 was determined by spectrophotometry. The results are shown in Table 8.

TABLE 8

| | time of dissolution | | |
| --- | --- | --- | --- |
| sample | 15 minutes | 45 minutes | 90 minutes |
| example 30 | 98.4 | 95.4 | 96.4 |
| example 31 | 96.8 | 92.4 | 96.9 |
| example 32 | 100.5 | 100.0 | 96.6 |
| example 33 | 93.0 | 94.4 | 90.1 |
| example 34 | 92.5 | 90.7 | 83.9 |
| example 35 | 90.6 | 90.2 | 86.5 |
| comparative example 14 | 0.0 | 1.3 | 13.6 |
| comparative example 15 | 10.0 | 41.4 | 57.6 |

The examples 30, 31, 33, 34, which are acidic solutions containing polyvinylpyrrolidone, and the examples 32 and 35, which are basic solutions containing polyvinylpyrrolidone, maintain good solubility as compared to the Comparative example 14, which is a water suspension, and the Comparative example 15, which is a basic solution.

TEST EXAMPLE 9

Oral Administration Test for Dogs (Oral Aqueous Solution)

For the samples, the compositions of examples 36, 37 and Comparative example 16 were used.

Male beagles (n=4 to 5 dogs) of weight 10-15 kg were fasted for approximately 17 hours from the day before drug administration. With the samples of examples 36 and 37, 10 mg/kg of T-5224 and with the sample of Comparative example 16, 30 mg/kg of T-5224 were administered orally. After administration, the dogs ingested 20 mL of water. Blood was collected periodically from the front leg vein, and after removing the protein from the obtained plasma with acetonitrile, the concentration of T-5224 was measured by the LC-MS/MS method. The area under the curve (AUC) value for the plasma concentration-time curve for 0 to 6 hours was determined. The unit for the AUC value is μg·hr/mL. The results are shown in Table 9.

TABLE 9

| sample | composition of administration | dose of administration (mg/kg) | AUC |
| --- | --- | --- | --- |
| example 36 | solution (alkaline) | 10 | 0.48 |
| example 37 | solution (acidic) | 10 | 0.49 |
| comparative example 16 | capsule filling of drug substance | 30 | 0.13 |

Compared to the Comparative example 16 in which a dosage of 30 mg/kg was administered orally, the oral solid compositions of the present invention (examples 36, 37) in which 10 mg/kg were administered orally had greatly increased AUC values.

Next, the present invention will be described giving examples and comparative examples. However, the present invention is not limited to these. In addition, in the examples and comparative examples of the oral solid compositions, T-5224 and L-arginine were both used as pulverized powder.

COMPARATIVE EXAMPLE 1

The following were weighed and mixed: 150 mg of T-5224; 2400 mg of directly compressible lactose (Tabletose 80 from Meggle Corp.); 52.5 mg of crospovidone (Kollidon CL from BASF Corp.); and 22.5 mg of magnesium stearate. This was screened with a 30 mesh screen and mixed to form tabletting powder. Tablets were formed from 175 mg of the tabletting powder with a punch having a diameter of 8.0 mm. This resulted in tablets with 10 mg T-5224 content.

COMPARATIVE EXAMPLE 2

The following were weighed and mixed: 150 mg of T-5224; 450 mg of polyvinylpyrrolidone K-30 (Plasdone K29/32 from ISP Corp.); 1950 mg of directly compressible lactose (Tabletose 80 from Meggle Corp.); 52.5 mg of crospovidone (Kollidon CL from BASF Corp.); and 22.5 mg of magnesium stearate. This was screened with a 30 mesh screen and mixed to form tabletting powder. Tablets were formed from 175 mg of the tabletting powder with a punch having a diameter of 8.0 mm. This resulted in tablets with 10 mg T-5224 content.

COMPARATIVE EXAMPLE 3

The following were weighed and mixed: 150 mg of T-5224; 450 mg of L-arginine (Ajinomoto Corp.); 1950 mg of directly compressible lactose (Tabletose 80 from Meggle Corp.); 52.5 mg of crospovidone (Kollidon CL from BASF Corp.); and 22.5 mg of magnesium stearate. This was screened with a 30 mesh screen and mixed to form tabletting powder. Tablets were formed from 175 mg of the tabletting powder with a punch having a diameter of 8.0 mm. This resulted in tablets with 10 mg T-5224 content.

COMPARATIVE EXAMPLE 4

The following were weighed and mixed: 100 mg of T-5224; 300 mg of polyvinylpyrrolidone K-30 (Plasdone K29/32 from ISP Corp.); 1000 mg of sodium bicarbonate; 1000 mg of β-cyclodextrin (Celldex B-100 from Nihon Shokuhin Kako Corp. Ltd.); 50 mg of crospovidone (Kollidon CL from BASF Corp.); and 25 mg of magnesium stearate. This was screened with a 30 mesh screen and mixed to form tabletting powder. Tablets were formed from 247.5 mg of the tabletting powder with a punch having a diameter of 8.5 mm. This resulted in tablets with 10 mg T-5224 content.

COMPARATIVE EXAMPLE 5

The following were weighed and mixed: 100 mg of T-5224; 300 mg of polyvinylpyrrolidone K-30 (Plasdone K29/32 from ISP Corp.); 600 mg of glycine; 1000 mg of β-cyclodextrin (Celldex B-100 from Nihon Shokuhin Kako Corp. Ltd.); 40 mg of crospovidone (Kollidon CL from BASF Corp.); and 20 mg of magnesium stearate. This was screened with a 30 mesh screen and mixed to form tabletting powder. Tablets were formed from 206 mg of the tabletting powder with a punch having a diameter of 8.5 mm. This resulted in tablets with 10 mg T-5224 content.

COMPARATIVE EXAMPLE 6

The following were weighed and mixed: 100 mg of T-5224; 300 mg of polyvinylpyrrolidone K-30 (Plasdone K29/32 from ISP Corp.); 600 mg of anhydrous dibasic calcium phosphate (Fujicalin SG from Fuji Kagaku); 1000 mg of β-cyclodextrin (Celldex B-100 from Nihon Shokuhin Kako Corp. Ltd.); 40 mg of crospovidone (Kollidon CL from BASF Corp.); and 20 mg of magnesium stearate. This was screened with a 30 mesh screen and mixed to form tabletting powder. Tablets were formed from 206 mg of the tabletting powder with a punch having a diameter of 8.5 mm. This resulted in tablets with 10 mg T-5224 content.

COMPARATIVE EXAMPLE 7

The following were weighed and mixed: 100 mg of T-5224; 300 mg of polyvinylpyrrolidone K-30 (Plasdone K29/32 from ISP Corp.); 600 mg of magnesium aluminometasilicate (Neusilin VS2 from Fuji Kagaku); 1000 mg of β-cyclodextrin (Celldex B-100 from Nihon Shokuhin Kako Corp. Ltd.); 40 mg of crospovidone (Kollidon CL from BASF Corp.); and 20 mg of magnesium stearate. This was screened with a 30 mesh screen and mixed to form tabletting powder. Tablets were formed from 206 mg of the tabletting powder with a punch having a diameter of 8.5 mm. This resulted in tablets with 10 mg T-5224 content.

COMPARATIVE EXAMPLE 8

T-5224 was screened through a 60 mesh screen, and 450 mg of the result was filled in size 000 capsules. This resulted in capsules with 450 mg T-5224 content.

COMPARATIVE EXAMPLE 9

The following were weighed and mixed: 100 mg of T-5224; 300 mg of L-arginine (Ajinomoto Corp.); 910 mg of directly compressible mannitol (Parteck M100 from Merck Corp.); 27 mg of sodium carboxymethyl starch (Primogel from Matsutani Corp.); and 14 mg of magnesium stearate. This was screened with a 30 mesh screen and mixed to form tabletting powder. Tablets were formed from 135 mg of the tabletting powder with a punch having a diameter of 7 mm. This resulted in tablets with 10 mg T-5224 content.

COMPARATIVE EXAMPLE 10

Ten milligrams of T-5224 was filled in size 4 capsules. This resulted in capsules with 10 mg T-5224 content.

COMPARATIVE EXAMPLE 11

Eight hundred milligrams of T-5224 was dissolved in 40 mL of 0.1 mol/L sodium hydroxide. To 4 mL of this solution was added 4 mL of purified water to obtain a solution with 10 mg/mL T-5224 content.

COMPARATIVE EXAMPLE 12

Eight hundred milligrams of T-5224 was dissolved in 40 mL of 0.1 mol/L sodium hydroxide. To 4 mL of this solution was dissolved 720 mg of hydroxypropylmethylcellulose (TC-5E from Shinetsu Kagaku), and then 4 mL of purified water was added. This resulted in a solution with 10 mg/mL T-5224 content.

COMPARATIVE EXAMPLE 13

Eight hundred milligrams of T-5224 was dissolved in 40 mL of 0.1 mol/L sodium hydroxide. To 4 mL of this solution was dissolved 720 mg of polyethylene glycol 6000, and then 4 mL of purified water was added. This resulted in a solution with 10 mg/mL T-5224 content.

COMPARATIVE EXAMPLE 14

Ten milligrams of T-5224 was suspended in 5 mL of purified water, resulting in a suspension with 10 mg T-5224 content.

COMPARATIVE EXAMPLE 15

In 5 mL of purified water was dissolved 12.7 mg of T-5224 tri sodium salt, resulting in an aqueous solution with 10 mg T-5224 content.

COMPARATIVE EXAMPLE 16

T-5224 was screened through a 60 mesh screen, and 450 mg of the result was used to fill size 000 capsules. This resulted in capsules with 450 mg T-5224 content.

EXAMPLE 1

The following were weighed and mixed: 150 mg of T-5224; 450 mg of polyvinylpyrrolidone K-30 (Plasdone K29/32 from ISP Corp.); 450 mg of L-arginine (Ajinomoto Corp.); 1500 mg of directly compressible lactose (Tabletose 80 from Meggle Corp.); 52.5 mg of crospovidone (Kollidon CL from BASF Corp.); and 22.5 mg of magnesium stearate. This was screened with a 30 mesh (500 micron openings) screen and mixed to form tabletting powder. Tablets were formed from 175 mg of the tabletting powder with a punch having a diameter of 8.0 mm. This resulted in tablets with 10 mg T-5224 content.

EXAMPLE 2

The following were weighed and mixed: 100 mg of T-5224; 300 mg of polyvinylpyrrolidone K-30 (Plasdone K29/32 from ISP Corp.); 600 mg of L-arginine (Ajinomoto Corp.); 1000 mg of β-cyclodextrin (Celldex B-100 from Nihon Shokuhin Kako Corp. Ltd.); 40 mg of crospovidone (Kollidon CL from BASF Corp.); and 20 mg of magnesium stearate. This was screened with a 30 mesh screen and mixed to form tabletting powder. Tablets were formed from 206 mg of the tabletting powder with a punch having a diameter of 8.5 mm. This resulted in tablets with 10 mg T-5224 content.

EXAMPLE 3

The following were weighed and mixed: 100 mg of T-5224; 300 mg of polyvinylpyrrolidone K-30 (Plasdone K29/32 from ISP Corp.); 600 mg of potassium carbonate; 1000 mg of β-cyclodextrin (Celldex B-100 from Nihon Shokuhin Kako Corp. Ltd.); 40 mg of crospovidone (Kollidon CL from BASF Corp.); and 20 mg of magnesium stearate. This was screened with a 30 mesh screen and mixed to form tabletting powder. Tablets were formed from 206 mg of the tabletting powder with a punch having a diameter of 8.5 mm. This resulted in tablets with 10 mg T-5224 content.

EXAMPLE 4

The following were weighed and mixed: 1.2 g of T-5224; 3.6 g of polyvinylpyrrolidone K-30 (Plasdone K29/32 from ISP Corp.); 7.2 g of L-arginine (Ajinomoto Corp.); 3.6 g of directly compressible lactose (Tabletose 80 from Meggle Corp.); 0.312 g of crospovidone (Kollidon CL from BASF Corp.); and 0.156 g of magnesium stearate. This was screened with a 30 mesh screen and mixed to form tabletting powder. Tablets were formed from 133.9 mg of the tabletting powder with a punch having a diameter of 7.5 mm. This resulted in tablets with 10 mg T-5224 content.

EXAMPLE 5

The following were weighed and mixed: 10 g of T-5224; 30 g of polyvinylpyrrolidone K-30 (Plasdone K29/32 from ISP Corp.); 30 g of L-arginine (Ajinomoto Corp.); 61.1 g of directly compressible lactose (Pharmatose DCL-14 from DMV Corp.); 2.6 g of sodium carboxymethyl starch (Primogel from Matsutani Corp.); and 1.3 g of magnesium stearate. This was screened with a 30 mesh screen and mixed to form tabletting powder. Tablets were formed from 135 mg of the tabletting powder with a punch having a diameter of 7.0 mm. This resulted in tablets with 10 mg T-5224 content.

EXAMPLE 6

The following were weighed and mixed: 1.2 g of T-5224; 3.6 g of polyvinylpyrrolidone K-30 (Plasdone K29/32 from ISP Corp.); 2.4 g of L-arginine (Ajinomoto Corp.); 8.4 g of directly compressible lactose (Tabletose 80 from Meggle Corp.); 0.312 g of crospovidone (Kollidon CL from BASF Corp.); and 0.156 g of magnesium stearate. This was screened with a 30 mesh screen and mixed to form tabletting powder. Tablets were formed from 133.9 mg of the tabletting powder with a punch having a diameter of 7.5 mm. This resulted in tablets with 10 mg T-5224 content.

EXAMPLE 7

The following were weighed and mixed: 1.2 g of T-5224; 3.6 g of polyvinylpyrrolidone K-30 (Plasdone K29/32 from ISP Corp.); 1.2 g of L-arginine (Ajinomoto Corp.); 9.6 g of directly compressible lactose (Tabletose 80 from Meggle Corp.); 0.312 g of Kollidon CL (from BASF Corp.); and 0.156 g of magnesium stearate. This was screened with a 30 mesh screen and mixed to form tabletting powder. Tablets were formed from 133.9 mg of the tabletting powder with a punch having a diameter of 7.5 mm. This resulted in tablets with 10 mg T-5224 content.

EXAMPLE 8

The following were weighed and mixed: 20 g of T-5224; moistened 10 g of polyvinylpyrrolidone K-30 (Plasdone K29/32 from ISP Corp.); moistened 60 g of L-arginine (Ajinomoto Corp.); 129.7 g of pulverized directly compressible mannitol (Parteck M100 from Merck Corp.); 4.6 g of sodium carboxymethyl starch (Primogel from Matsutani Corp.); and 5.8 g of magnesium stearate. This was screened with a 30 mesh screen and mixed to form tabletting powder. Tablets were formed from the tabletting powder with a punch having a diameter of 6.5 mm. This was then dried at 40 deg C. and resulted in tablets with tablet weight of 115 mg with 10 mg T-5224 content.

EXAMPLE 9

The following were weighed and mixed: 20 g of T-5224; moistened 20 g of polyvinylpyrrolidone K-30 (Plasdone K29/32 from ISP Corp.); moistened 60 g of L-arginine (Ajinomoto Corp.); 119.6 g of pulverized directly compressible mannitol (Parteck M100 from Merck Corp.); 4.6 g of sodium carboxymethyl starch (Primogel from Matsutani Corp.); and 5.8 g of magnesium stearate. This was screened with a 30 mesh screen and mixed to form tabletting powder. Tablets were formed from the tabletting powder with a punch having a diameter of 6.5 mm. This was then dried at 40 deg C. and resulted in tablets with tablet weight of 115 mg with 10 mg T-5224 content.

EXAMPLE 10

The following were weighed and mixed: 20 g of T-5224; moistened 60 g of polyvinylpyrrolidone K-30 (Plasdone K29/32 from ISP Corp.); moistened 60 g of L-arginine (Ajinomoto Corp.); 79.6 g of pulverized directly compressible mannitol (Parteck M100 from Merck Corp.); 4.6 g of sodium carboxymethyl starch (Primogel from Matsutani Corp.); and 5.8 g of magnesium stearate. This was screened with a 30 mesh screen and mixed to form tabletting powder. Tablets were formed from the tabletting powder with a punch having a diameter of 6.5 mm. This was then dried at 40 deg C. and resulted in tablets with tablet weight of 115 mg with 10 mg T-5224 content.

EXAMPLE 11

The following were weighed and mixed: 10 g of T-5224; moistened 3 g of polyvinylpyrrolidone K-30 (Plasdone K29/32 from ISP Corp.); moistened 30 g of L-arginine (Ajinomoto Corp.); 67.4 g of pulverized directly compressible mannitol (Parteck M100 from Merck Corp.); 2.3 g of sodium carboxymethyl starch (Primogel from Matsutani Corp.); and 2.3 g of magnesium stearate. This was screened with a 30 mesh screen and mixed to form tabletting powder. Tablets were formed from the tabletting powder with a punch having a diameter of 6.5 mm. This was then dried at 40 deg C. and resulted in tablets with tablet weight of 115 mg with 10 mg T-5224 content.

EXAMPLE 12

The following were weighed and mixed: 100 mg of T-5224; 300 mg of polyvinylpyrrolidone K-25 (Plasdone K25 from ISP Corp.); 600 mg of L-arginine (Ajinomoto Corp.); 1000 mg of β-cyclodextrin (Celldex B-100 from Nihon Shokuhin Kako Corp. Ltd.); 40 mg of crospovidone (Kollidon CL from BASF Corp.); and 20 mg of magnesium stearate. This was screened with a 30 mesh screen and mixed to form tabletting powder. Tablets were formed from 206 mg of the tabletting powder with a punch having a diameter of 8.5 mm. This resulted in tablets with 10 mg T-5224 content.

EXAMPLE 13

The following were weighed and mixed: 1.2 g of T-5224; 3.6 g of polyvinylpyrrolidone K-17 (Kollidon 17 PF from BASF Corp.); 2.4 g of L-arginine (Ajinomoto Corp.); 8.4 g of directly compressible mannitol (Parteck M100 from Merck Corp.); 0.312 g of crospovidone (Kollidon CL from BASF Corp.); and 0.156 g of magnesium stearate. This was screened with a 30 mesh screen and mixed to form tabletting powder. Tablets were formed from 133.9 mg of the tabletting powder with a punch having a diameter of 7.5 mm. This resulted in tablets with 10 mg T-5224 content.

EXAMPLE 14

The following were weighed and mixed: 1.2 g of T-5224; 3.6 g of polyvinylpyrrolidone K-30 (Plasdone K29/32 from ISP Corp.); 3.6 g of L-arginine (Ajinomoto Corp.); 3.6 g of directly compressible lactose (Tabletose 80 from Meggle Corp.); 3.6 of β-cyclodextrin (Celldex B-100 from Nihon Shokuhin Kako Corp. Ltd.); 0.312 g of crospovidone (Kollidon CL from BASF Corp.); and 0.156 g of magnesium stearate. This was screened with a 30 mesh screen and mixed to form tabletting powder. Tablets were formed from 133.9 mg of the tabletting powder with a punch having a diameter of 7.5 mm. This resulted in tablets with 10 mg T-5224 content.

EXAMPLE 15

The following were weighed and mixed: 100 mg of T-5224; 300 mg of polyvinylpyrrolidone K-30 (Plasdone K29/32 from ISP Corp.); 300 mg of L-arginine (Ajinomoto Corp.); 300 mg of β-cyclodextrin (Celldex B-100 from Nihon Shokuhin Kako Corp. Ltd.); 20 mg of sodium carboxymethyl starch (Primogel from Matsutani Corp.); and 10 mg of magnesium stearate. This was screened with a 30 mesh screen and mixed to form tabletting powder. Tablets were formed from 103 mg of the tabletting powder with a punch having a diameter of 6.5 mm. This resulted in tablets with 10 mg T-5224 content.

EXAMPLE 16

The following were weighed and mixed: 5 g of T-5224; 5 g of polyvinylpyrrolidone K-30 (Plasdone K29/32 from ISP Corp.); 15 g of L-arginine (Ajinomoto Corp.); 1.68 g of directly compressible mannitol (Parteck M100 from Merck Corp.); 0.55 g of sodium carboxymethyl starch (Primogel from Matsutani Corp.); and 0.28 g of magnesium stearate. This was screened with a 30 mesh screen and mixed to form a mixed powder. The mixed powder was granulated by dry granulation, resulting in T-5224 granules.

EXAMPLE 17

The following were weighed and mixed: 2 g of T-5224; 2 g of polyvinylpyrrolidone K-30 (Plasdone K29/32 from ISP Corp.); 6 g of L-arginine (Ajinomoto Corp.); 12.1 g of pulverized directly compressible mannitol (Parteck M100 from Merck Corp.); 0.5 g of sodium carboxymethyl starch (Primogel from Matsutani Corp.); and 0.5 g of magnesium stearate.

This was screened with a 30 mesh screen and mixed to form a mixed powder. A circular capsule filler was used to fill size 2 capsules with 230 mg of the mixed powder, resulting in capsules with 20 mg T-5224 content.

EXAMPLE 18

The following were weighed and mixed: 2 g of T-5224; 2 g of polyvinylpyrrolidone K-30 (Plasdone K29/32 from ISP Corp.); 6 g of L-arginine (Ajinomoto Corp.); 12.1 g of corn starch; 0.5 g of sodium carboxymethyl starch (Primogel from Matsutani Corp.); and 0.5 g of magnesium stearate. This was screened with a 30 mesh screen and mixed to form a mixed powder. A circular capsule filler was used to fill size 2 capsules with 230 mg of the mixed powder, resulting in capsules with 20 mg T-5224 content.

EXAMPLE 19

The following were weighed and mixed: 8 g of T-5224; 8 g of polyvinylpyrrolidone K-30 (Plasdone K29/32 from ISP Corp.); 24 g of L-arginine (Ajinomoto Corp.); 0.8 g of sodium carboxymethyl starch (Primogel from Matsutani Corp.); and 0.8 g of magnesium stearate. This was screened with a 30 mesh screen and mixed to form a mixed powder. A circular capsule filler was used to fill size 0 capsules with 416 mg of the mixed powder, resulting in capsules with 80 mg T-5224 content.

EXAMPLE 20

The following were weighed and mixed: 4 g of T-5224; 4 g of polyvinylpyrrolidone K-30 (Plasdone K29/32 from ISP Corp.); 12 g of L-arginine (Ajinomoto Corp.); 24.2 g of pulverized directly compressible mannitol (Parteck M100 from Merck Corp.); 0.9 g of sodium carboxymethyl starch (Primogel from Matsutani Corp.); and 0.9 g of magnesium stearate. This was screened with a 30 mesh screen and mixed to form a mixed powder. A circular capsule filler was used to fill size 0 capsules with 460 mg of the mixed powder, resulting in capsules with 40 mg T-5224 content.

EXAMPLE 21

The following were weighed and mixed: 1 g of T-5224; moistened 1 g of polyvinylpyrrolidone K-30 (Plasdone K29/32 from ISP Corp.); moistened 3 g of L-arginine (Ajinomoto Corp.); 0.1 g of sodium carboxymethyl starch (Primogel from Matsutani Corp.); and 0.1 g of magnesium stearate. This was screened with a 30 mesh screen and mixed to form tabletting powder. Tablets were formed from the tabletting powder with a punch having a diameter of 10 mm. This was then dried at 40 deg C., resulting in tablets with a tablet weight of 416 mg with 80 mg T-5224 content.

EXAMPLE 22

The following were weighed and mixed: 10 g of T-5224; moistened 10 g of polyvinylpyrrolidone K-30 (Plasdone K29/32 from ISP Corp.); moistened 30 g of L-arginine (Ajinomoto Corp.); 1 g of sodium carboxymethyl starch (Primogel from Matsutani Corp.); and 1 g of magnesium stearate. This was screened with a 30 mesh screen and mixed to form tabletting powder. Tablets were formed from the tabletting powder with a punch having a diameter of 8.5 mm. This was then dried at 40 deg C., resulting in tablets with a tablet weight of 208 mg with 40 mg T-5224 content.

EXAMPLE 23

The following were weighed and mixed: 106 mg of T-5224 ammonium salt; 300 mg of polyvinylpyrrolidone K-30 (Plasdone K29/32 from ISP Corp.); 300 mg of L-arginine (Ajinomoto Corp.); 1000 mg of directly compressible lactose (Tabletose 80 from Meggle Corp.); 40 mg of crospovidone (Kollidon CL from BASF Corp.); and 20 mg of magnesium stearate. This was screened with a 30 mesh screen and mixed to form tabletting powder. Tablets were formed from 176.6 mg of the tabletting powder with a punch having a diameter of 8 mm. This resulted in T-5224 ammonium salt tablets (with 10 mg T-5224 content).

EXAMPLE 24

The following were weighed and mixed: 1 g of T-5224; 3 g of polyvinylpyrrolidone K-30 (Plasdone K29/32 from ISP Corp.); 10 g of L-arginine (Ajinomoto Corp.); 10 g of hydroxypropyl-β-cyclodextrin (Celldex HP-β-CD from Nihon Shokuhin Kako Corp. Ltd.); 0.48 g of crospovidone (Kollidon CL from BASF Corp.); and 0.24 g of magnesium stearate. This was screened with a 30 mesh screen and mixed to form tabletting powder. Tablets were formed from 247.2 mg of the tabletting powder with a punch having a diameter of 8.5 mm. This resulted in tablets with 10 mg T-5224 content.

EXAMPLE 25

The following were weighed and mixed: 50 g of T-5224; moistened 50 g of polyvinylpyrrolidone K-30 (Plasdone K29/32 from ISP Corp.); moistened 150 g of L-arginine (Ajinomoto Corp.); 302 g of pulverized directly compressible mannitol (Parteck M100 from Merck Corp.); 11.5 g of sodium carboxymethyl starch (Primogel from Matsutani Corp.); and 11.5 g of magnesium stearate. This was screened with a 30 mesh screen and mixed to form tabletting powder. Tablets were formed from the tabletting powder with a punch having a diameter of 8.5 mm. This was then dried at 40 deg C. and resulted in tablets with tablet weight of 230 mg with 20 mg T-5224 content.

EXAMPLE 26

The following were weighed and mixed: 20 g of T-5224; 21.5 g of polyvinylpyrrolidone K-30 (Plasdone K29/32 from ISP Corp.); moistened 73.0 g of L-arginine (Ajinomoto Corp.); 121.5 g of pulverized directly compressible mannitol (Parteck M100 from Merck Corp.); 4.7 g of sodium carboxymethyl starch (Primogel from Matsutani Corp.); and 4.6 g of magnesium stearate. This was screened with a 30 mesh screen and mixed to form tabletting powder. Tablets were formed from the tabletting powder with a punch having a diameter of 8.5 mm. This was then dried at 50 deg C. and resulted in tablets with tablet weight of 230 mg with 20 mg T-5224 content.

EXAMPLE 27

Eight hundred milligrams of T-5224 was dissolved in 40 mL of 0.1 mol/L sodium hydroxide. To 4 mL of this solution was dissolved 240 mg of polyvinylpyrrolidone K-30 (Plasdone K29/32 from ISP Corp.), and then 4 mL of purified water was added to obtain a solution with 10 mg/mL T-5224 content.

EXAMPLE 28

Eight hundred milligrams of T-5224 was dissolved in 40 mL of 0.1 mol/L sodium hydroxide. To 4 mL of this solution was dissolved 480 mg of polyvinylpyrrolidone K-30 (Plasdone K29/32 from ISP Corp.), and then 4 mL of purified water was added to obtain a solution with 10 mg/mL T-5224 content.

EXAMPLE 29

Eight hundred milligrams of T-5224 was dissolved in 40 mL of 0.1 mol/L sodium hydroxide. To 4 mL of this solution was dissolved 720 mg of polyvinylpyrrolidone K-30 (Plasdone K29/32 from ISP Corp.), and then 4 mL of purified water was added to obtain a solution with 10 mg/mL T-5224 content.

EXAMPLE 30

One hundred sixty milligrams of T-5224 was dissolved in 8 mL of 0.1 mol/L sodium hydroxide. To this solution was dissolved 480 mg of polyvinylpyrrolidone K-30 (Plasdone K29/32 from ISP Corp.), and then 8 mL of 0.1 mol/L hydrochloric acid was added to obtain a solution with 10 mg/mL T-5224 content with a pH of 3.5.

EXAMPLE 31

One hundred sixty milligrams of T-5224 was dissolved in 8 mL of 0.1 mol/L sodium hydroxide. To this solution was dissolved 480 mg of polyvinylpyrrolidone K-30 (Plasdone K29/32 from ISP Corp.), and then 8 mL of 0.1 mol/L tartaric acid was added to obtain a solution with 10 mg/mL T-5224 content with a pH of 3.2.

EXAMPLE 32

One hundred sixty milligrams of T-5224 was dissolved in 8 mL of 0.1 mol/L sodium hydroxide. To this solution was dissolved 480 mg of polyvinylpyrrolidone K-30 (Plasdone K29/32 from ISP Corp.), and then 5 mL of purified water was added to 5 mL of this solution to obtain a solution with 10 mg/mL T-5224 content with a pH of 10.8.

EXAMPLE 33

One hundred sixty milligrams of T-5224 was dissolved in 8 mL of 10 mg/mL L-arginine aqueous solution. To this solution was dissolved 480 mg of polyvinylpyrrolidone K-30 (Plasdone K29/32 from ISP Corp.), and then 8 mL of 0.1 mol/L hydrochloric acid was added to obtain a solution with 10 mg/mL T-5224 content with a pH of 5.2.

EXAMPLE 34

One hundred sixty milligrams of T-5224 was dissolved in 8 mL of 10 mg/mL L-arginine aqueous solution. To this solution was dissolved 480 mg of polyvinylpyrrolidone K-30 (Plasdone K29/32 from ISP Corp.), and then 8 mL of 0.1 mol/L tartaric acid was added to obtain a solution with 10 mg/mL T-5224 content with a pH of 3.3.

EXAMPLE 35

One hundred sixty milligrams of T-5224 was dissolved in 8 mL of 20 mg/mL L-arginine aqueous solution. To this solution was dissolved 480 mg of polyvinylpyrrolidone K-30 (Plasdone K29/32 from ISP Corp.), and then 8 mL of purified water was added to obtain a solution with 10 mg/mL T-5224 content with a pH of 8.8.

EXAMPLE 36

One gram of T-5224 was dissolved in 50 mL of 0.1 mol/L sodium hydroxide. Three grams of polyvinylpyrrolidone K-30 (Plasdone K29/32 from ISP Corp.) was dissolved in this solution, and then 50 mL of purified water was added to obtain a solution with 10 mg/mL T-5224 content with a pH of 10.8.

EXAMPLE 37

One gram of T-5224 was dissolved in 50 mL of 0.1 mol/L sodium hydroxide. Three grams of polyvinylpyrrolidone K-30 (Plasdone K29/32 from ISP Corp.) was dissolved in this solution, and then 27 mL of 0.3 mol/L hydrochloric acid and 23 mL of purified water were added to obtain a solution with 10 mg/mL T-5224 content with a pH of 1.6.

EXAMPLE 38

Two grams of T-5224 was dissolved in 15.5 mL of 0.5 mol/L sodium hydroxide and 3.5 mL of purified water. Purified water was added to 10 mL of this solution to obtain 100 mL. Then, purified water was further added to 10 mL of this solution to obtain 100 mL. In 30 mL of this solution, 90 mg of polyvinylpyrrolidone K-30 (Plasdone K29/32 from ISP Corp.) was dissolved to obtain a solution with 1 mg/mL T-5224 content with a pH of 7.5.

EXAMPLE 39

Two grams of T-5224 was dissolved in 15.5 mL of 0.5 mol/L sodium hydroxide and 3.5 mL of purified water. Purified water was added to 10 mL of this solution to obtain 100 mL. Then, purified water was further added to 10 mL of this solution to obtain 100 mL. Then, purified water was further added to 10 mL of this solution to obtain 100 mL. In this solution, 30 mg of polyvinylpyrrolidone K-30 (Plasdone K29/32 from ISP Corp.) was dissolved to obtain a solution with 0.1 mg/mL T-5224 content with a pH of 7.0.

EXAMPLE 40

One gram of T-5224 was dissolved in 43 mL of 0.1 mol/L sodium hydroxide. In this solution, 3 g of polyvinylpyrrolidone K-30 (Plasdone K29/32 from ISP Corp.) was dissolved. To this solution was added 2.5 mL of 1 mol/L hydrochloric acid to obtain a solution with 20 mg/mL T-5224 content with a pH of 5.9.

EXAMPLE 41

0.5 grams of T-5224 was dissolved in 3.9 mL of 0.5 mol/L sodium hydroxide and 5.1 mL of purified water. In this solution, 1.5 g of polyvinylpyrrolidone K-30 (Plasdone K29/32 from ISP Corp.) was dissolved to obtain a solution with 50 mg/mL T-5224 content with a pH of 8.3.

EXAMPLE 42

0.5 grams of T-5224 and 0.5 g of L-arginine were dissolved in 9 mL of purified water. In this solution, 1.5 g of polyvinylpyrrolidone K-30 (Plasdone K29/32 from ISP Corp.) was dissolved and 0.8 mL of 1 mol/L hydrochloric acid solution was added to obtain a solution with 50 mg/mL T-5224 content with a pH of 7.8.

EXAMPLE 43

One gram of T-5224 was dissolved in 7.7 mL of 0.5 mol/L sodium hydroxide and 10 mL of purified water. In this solution, 0.5 g of polyvinylpyrrolidone K-30 (Plasdone K29/32 from ISP Corp.) was dissolved to obtain a solution with 50 mg/mL T-5224 content with a pH of 9.3.

EXAMPLE 44

One gram of T-5224 was dissolved in 7.7 mL of 0.5 mol/L sodium hydroxide and 10 mL of purified water. In this solution, 1 g of polyvinylpyrrolidone K-30 (Plasdone K29/32 from ISP Corp.) was dissolved to obtain a solution with 50 mg/mL T-5224 content with a pH of 9.0.

EXAMPLE 45

One gram of T-5224 was dissolved in 7.7 mL of 0.5 mol/L sodium hydroxide and 10 mL of purified water. In this solution, 1.5 g of polyvinylpyrrolidone K-30 (Plasdone K29/32 from ISP Corp.) was dissolved to obtain a solution with 50 mg/mL T-5224 content with a pH of 8.7.

EXAMPLE 46

One gram of T-5224 was dissolved in 7.7 mL of 0.5 mol/L sodium hydroxide and 10 mL of purified water. In this solution, 2 g of polyvinylpyrrolidone K-30 (Plasdone K29/32 from ISP Corp.) was dissolved to obtain a solution with 50 mg/mL T-5224 content with a pH of 8.4.

EXAMPLE 47

One gram of T-5224 was dissolved in 7.7 mL of 0.5 mol/L sodium hydroxide and 10 mL of purified water. In this solution, 3 g of polyvinylpyrrolidone K-30 (Plasdone K29/32 from ISP Corp.) was dissolved to obtain a solution with 50 mg/mL T-5224 content with a pH of 8.1.

EXAMPLE 48

Two grams of T-5224 was dissolved in 15.5 mL of 0.5 mol/L sodium hydroxide. In this solution, 2 g of polyvinylpyrrolidone K-30 (Plasdone K29/32 from ISP Corp.) was dissolved to obtain a solution with 100 mg/mL T-5224 content with a pH of 9.6.

EXAMPLE 49

Two grams of T-5224 was dissolved in 15.5 mL of 0.5 mol/L sodium hydroxide. In this solution, 4 g of polyvinylpyrrolidone K-30 (Plasdone K29/32 from ISP Corp.) was dissolved to obtain a solution with 100 mg/mL T-5224 content with a pH of 8.8.

EXAMPLE 50

Two grams of T-5224 was dissolved in 7.7 mL of 1 mol/L sodium hydroxide. In this solution, 1 g of polyvinylpyrrolidone K-30 (Plasdone K29/32 from ISP Corp.) was dissolved to obtain a solution with 200 mg/mL T-5224 content with a pH of 10.0.

EXAMPLE 51

Two grams of T-5224 was dissolved in 7.7 mL of 1 mol/L sodium hydroxide. In this solution, 2 g of polyvinylpyrrolidone K-30 (Plasdone K29/32 from ISP Corp.) was dissolved to obtain a solution with 200 mg/mL T-5224 content with a pH of 9.4.

INDUSTRIAL APPLICABILITY

A T-5224 oral composition containing polyvinylpyrrolidone according to the present invention can be produced with simple steps without requiring new manufacturing equipment. It maintains stable solubility even with changes in the pH of the gastrointestinal tract and of which gastrointestinal tract absorption is improved.

The invention claimed is:

1. An oral solid composition comprising 3-{5-[4-(cyclopentyloxy)-2-hydroxybenzoyl]-2-[(3-hydroxy-1,2-benzisoxazol-6-yl)methoxy]phenyl}propionic acid or a salt thereof; polyvinylpyrrolidone; and a basic material of which the 5 w/v % aqueous solution has the pH of 10 or more.

2. The oral solid composition according to claim 1, wherein the basic material of which the 5 w/v % aqueous solution has the pH of 10 or more is L-arginine or potassium carbonate.

3. The oral solid composition according to claim 1, wherein the basic material of which the 5 w/v % aqueous solution has the pH of 10 or more is L-arginine.

4. The oral solid composition according to any one of claim 1 to claim 4, wherein the oral solid composition contains a water-soluble excipient.

5. The oral solid composition according to claim 1, wherein the oral solid composition is a tablet or a capsule.

6. The oral solid composition according to claim 1, wherein the oral solid composition is a tablet.

7. An oral aqueous solution comprising 3-{5-[4-(cyclopentyloxy)-2-hydroxybenzoyl]-2-[(3-hydroxy-1,2-benzisoxazol-6-yl)methoxy]phenyl}propionic acid or a salt thereof and polyvinylpyrrolidone.

8. The oral aqueous solution according to claim 7, wherein the concentration of 3-{5-[4-(cyclopentyloxy)-2-hydroxybenzoyl]-2-[(3-hydroxy-1,2-benzisoxazol-6-yl)methoxy]phenyl}propionic acid is 0.01-20 w/v %.

9. The oral aqueous solution according to claim 7 or claim 8, wherein the amount of polyvinylpyrrolidone is 1-10 times per that of 3-{5-[4-(cyclopentyloxy)-2-hydroxybenzoyl]-2-[(3-hydroxy-1,2-benzisoxazol-6-yl)methoxy]phenyl}propionic acid.

10. The oral aqueous solution according to claim 7, wherein the pH of the oral aqueous solution is 3 to 9.

11. The oral solid composition according to claim 2, wherein the oral solid composition is a tablet or a capsule.

12. The oral solid composition according to claim 3, wherein the oral solid composition is a tablet or a capsule.

13. The oral solid composition according to claim 2, wherein the oral solid composition is a tablet.

14. The oral solid composition according to claim 3, wherein the oral solid composition is a tablet.

15. The oral aqueous solution according to claim 8, wherein the pH of the oral aqueous solution is 3 to 9.

16. The oral aqueous solution according to claim 9, wherein the pH of the oral aqueous solution is 3 to 9.

* * * * *